United States Patent [19]

Like et al.

[11] 4,336,151

[45] Jun. 22, 1982

[54] DISINFECTANT/CLEANSER COMPOSITIONS EXHIBITING REDUCED EYE IRRITANCY POTENTIAL

[75] Inventors: Burton M. Like, East Brunswick; Dennis Smialowicz, Waldwick; Eugene Brandli, Towaco, all of N.J.

[73] Assignee: American Cyanamid Company, Stamford, Conn.

[21] Appl. No.: 280,657

[22] Filed: Jul. 6, 1981

[51] Int. Cl.³ .................... C11D 3/48; A01N 33/12; C11D 1/835
[52] U.S. Cl. ................................. 252/106; 424/329; 252/139; 252/173; 252/174.17; 252/174.25; 252/528; 252/DIG. 5; 252/DIG. 14
[58] Field of Search ............... 424/329; 252/106, 139, 252/173, 174.17, 174.25, 528, DIG. 5, DIG. 14

[56] References Cited

U.S. PATENT DOCUMENTS

| 2,577,773 | 12/1951 | Lambert | 424/329 |
| 3,156,656 | 11/1964 | Libby | 252/106 |
| 3,402,242 | 9/1968 | Laumann | 424/329 |
| 4,013,576 | 3/1977 | Loshack | 424/329 |

Primary Examiner—Sam Silverberg
Attorney, Agent, or Firm—William H. Calnan

[57] ABSTRACT

Disinfectant/cleanser compositions retaining broad spectrum germicidal activity but exhibiting significantly reduced eye irritancy potential comprise a quaternary ammonium compound, a non-ionic surfactant, d-limonene, an eye irritancy reducing compound, water, and optionally a lower aliphatic alcohol.

16 Claims, No Drawings

DISINFECTANT/CLEANSER COMPOSITIONS EXHIBITING REDUCED EYE IRRITANCY POTENTIAL

This invention relates generally to disinfectant/cleanser compositions for hard surface soil and stain removal. More particularly, it relates to such compositions which possess broad spectrum germicidal efficacy, contain d-limonene which acts as a fragrance and a soil and stain remover, and further include certain compounds, hereinafter referred to as "mitigants", which reduce the ocular irritancy potential of the compositions. In addition to the foregoing components, the compositions also contain a quaternary ammonium compound, a non-ionic surfactant, water, and, optionally, a lower aliphatic alcohol.

Disinfectant/cleanser compositions containing d-limonene as a soil and stain remover are well known. Incorporation into such compositions of a quaternary ammonium compound and, to a lesser extent, a non-ionic surfactant imparts a broad spectrum germicidal activity thereto, i.e., the composition is effective in killing both gram positive and gram negative organisms. However, the quaternary ammonium compound has a rather irritating effect on the eye, as disclosed by the Draize Test on white albino rabbits. (See "Principles and Procedures for Evaluating the Toxicity of Household Products," National Academy of Science Publication 1138 (1977).) The surfactant also contributes to the irritancy of the composition, albeit generally to a lesser degree.

While various attempts have been made to reduce the eye irritancy of these disinfectant/cleanser compositions, such as by reducing the concentration of the quaternary ammonium compound and/or the non-ionic surfactant, none has satisfactorily done so without concommitantly impairing the germicidal efficacy of the compositions.

Accordingly, it is an object of the instant invention to provide disinfectant/cleanser compositions exhibiting broad spectrum germicidal activity which have significantly reduced eye irritancy potential.

It has been discovered that the foregoing object may be achieved by incorporating into a d-limonene-containing broad spectrum germicidally active composition, an effective amount of a compound which significantly mitigates the eye irritation of said composition when evaluated according to the aforementioned Draize Test.

The mitigants of the present invention are:

1. Ethoxylated cocodiethanolamide which contain a sufficient amount of condensed ethylene oxide such that the eye irritancy of the composition is significantly reduced. Preferably, the ethoxylated cocodiethanolamide contains at least about three moles of condensed ethylene oxide. Most preferably, the ethoxylated cocodiethanolamide contains about 5 moles of condensed ethylene oxide. (An ethoxylated cocodiethanolamide containing about 5 moles of condensed ethylene oxide may be commercially purchased under the name Unamide® C5 made by Lonza Chemical Co.);

2. Polyoxyethylene which contains a sufficient amount of condensed ethylene oxide such that the eye irritancy of the composition is significantly reduced. Preferably, the polyoxyethylene contains at least about 40 moles of condensed ethylene oxide. Most preferably, the polyoxyethylene contains from about 100 to 175 moles of condensed ethylene oxide. (Polyoxyethylene compounds containing various amounts of condensed ethylene oxide are available from Union Carbide Corp. under the Carbowax® trademark);

3. Ethoxylated lanolin which contains a sufficient amount of condensed ethylene oxide such that the eye irritancy of the composition is significantly reduced. Preferably, the ethoxylated lanolin contains at least about 30 moles of condensed ethylene oxide. Most preferably, the ethoxylated lanolin contains from about 100 to 175 moles of condensed ethylene oxide. (An ethoxylated lanolin containing about 150 moles of condensed ethylene oxide is available under the name Solulan® L-575 from Americhol Chemical Co.);

4. Hydrolyzed animal protein, such as Lanasan® CL, made by Sandoz Chemical Co.;

5. Allantoin;

6. 1,6-hexylene glycol;

7. Stearyl dimethylamine oxide, such as Ammonyx® SO, made by Onyx Chemical Co.;

8. Dextrose sugar, such as 2001 Cerelose, made by CPC International, Inc.; and

9. Imidazole

The mitigant is used in the composition in an amount sufficient to significantly reduce the eye irritation potential thereof. Generally, the mitigant comprises about 0.1 to 5%, by weight, of the composition, with about 1 to 3%, by weight, preferred. The amount used, however, will vary depending upon, inter alia, the irritancy levels of the other ingredients in the composition. Accordingly, the optimum amount of the mitigant to be included in a given "base" formulation will best be determined by routine experimentation. Obviously, mixtures of two or more of the mitigants may be used, provided there is no deleterious interaction between them.

As stated above, the quaternary ammonium compounds used in disinfectant/cleanser compositions are generally the primary irritants, the extent of the eye irritation increasing with increasing concentration. The non-ionic surfactant behaves similarly, although its contribution to irritation is generally not as great as that of the quaternary ammonium compound. However, there is apparently no synergistic irritation effect brought about by the combination of the quaternary ammonium compound and the non-ionic surfactant.

Quaternary ammonium compounds useful in the composition of the instant invention include long chain ($C_8$–$C_{12}$) dialkyldimethyl ammonium chlorides, such as dioctyldimethyl ammonium chloride and didecyldimethyl ammonium chloride, or mixtures thereof, and n-alkyl ($C_{12}$–$C_{18}$) dimethylbenzyl and n-alkyldimethylethylbenzyl ammonium chlorides. Bardac 20 (Lonza) is a preferred long chain dialkyldimethyl ammonium chloride and comprises about 25%, by weight, dioctyl-, 25% didecyl-, and 50% octyldecyldimethyl ammonium chlorides. BTC 2125 (Onyx) is a preferred n-alkyldimethylbenzyl ammonium chloride comprising about 50%, by weight, $C_{12}$–$C_{18}$ alkyldimethylbenzyl ammonium chlorides and 50% $C_{12}$–$C_{18}$ alkyldimethylethylbenzyl ammonium chlorides. The quaternary ammonium compound is generally present in the composition in an amount equal to about 3 to 10%, by weight, with about 3 to 6%, by weight, preferred.

The non-ionic surfactants used in the formulation of this invention include, but are not limited to, that class of compounds formed by condensation of an alkyl phenol, an alkyl amine, an aliphatic alcohol, or a fatty acid with sufficient ethylene oxide to produce a compound having a polyethylene chain within the molecule, i.e., a chain composed of recurring (—O—CH$_2$—CH$_2$—) groups. Many compounds of this type are known. Exemplary of this type of surfactant are those compounds produced by condensing about 5–30, preferably about 8–16, moles of ethylene oxide with one mole of (1) an alkyl phenol having about 0–15, preferably 7–10, carbon atoms in the alkyl group; (2) an alkyl amine having about 10–20, preferably 12–16, carbon atoms in the alkyl group; (3) an aliphatic alcohol having about 9–20, preferably 12–16, carbon atoms in its molecule; and (4) a fatty acid having about 10–20, preferably 12–16, carbon atoms in its molecule. Preferred nonionic surfactants include Neodol 25-9 (Shell Chemical Co.), which is an ethoxylated mixture of normal and 2-methyl branched primary C$_{12-15}$ alcohols having about 9 moles of condensed ethylene oxide, and Triton X100 (Rohm & Haas), which is an octylphenol having about 9 moles of condensed ethylene oxide. The non-ionic surfactant typically comprises about 1 to 10%, by weight, of the composition, with about 3 to 8%, by weight, preferred.

Generally, the most germicidally efficacious compositions contain non-ionic surfactant and quaternary ammonium compound in a ratio from about 0.5:1 to 8:1. Preferably, the ratio is from about 2:1 to 4:1. This is so because the presence of too much non-ionic surfactant tends to interfere with the germ killing effectiveness of the quaternary ammonium compound. However, in large part this will depend upon the mix of ingredients used. It will therefore be understood that the optimum ratio of nonionic surfactant to quaternary ammonium compound in a given formulation is best determined by routine experimentation.

The d-limonene which is incorporated into the composition functions as a fragrance and as a soil and stain remover. As a fragrance, its citrus scent simply imparts a pleasant odor to the composition. As a soil and stain remover, the grease cutting capability of d-limonene is well known. Typically, the d-limonene comprises about 0.25 to 6%, by weight, of the composition, with about 3 to 5%, by weight, preferred.

Optionally a lower aliphatic (C$_1$–C$_3$) alcohol may be incorporated into the composition, its purpose being to stabilize the composition at extreme temperatures and to reduce its viscosity. When used, the alcohol is generally present in an amount from about 1 to 6% by weight, of the composition, with about 2 to 4%, by weight, preferred.

The remainder of the composition comprises water, and may contain other additives, such as dyes, UV stabilizers, and the like.

The formulations of the present invention pass the Association of Official Analytical Chemists (A.O.A.C.). Use-Dilution Test, which appears in the A.O.A.C. Methods Manual, 13th edition (1980), at a rate whch gives statistical confidence at the 95% level as compared to known compositions which use a quaternary ammonium compound to provide broad spectrum germicidal activity.

The following examples are illustrative of the present invention, but are in no way to be construed as a limitation thereof. All parts and percentages are by weight unless otherwise noted.

EXAMPLE 1

A broad spectrum germicidally active disinfectant/cleanser composition having substantially reduced eye irritancy potential is prepared having the following ingredients:

|  | Percent |
| --- | --- |
| Quaternary Ammonium Compound* | 3.0 |
| Non-ionic surfactant** | 8.0 |
| d-limonene | 3.5 |
| Builder*** | 3.5 |
| Dye (1% solution) | 0.1 |
| Stearyl dimethylamine oxide | 0.5 |
| Water | qs to 100 |

Note:
*Bardac 20
**Triton X 100
***Potassium Carbonate

EXAMPLE 2

This example illustrates the effectiveness of the several mitigants of the present invention.

A control composition, containing no mitigant, was prepared having the following ingredients:

|  | Percent |
| --- | --- |
| Quaternary Ammonium Compound* | 3.5 |
| Non-ionic surfactant** | 7.0 |
| d-limonene | 3.0 |
| Ethanol (190 proof) | 3.0 |
| Builder*** | 3.5 |
| Dye (0.5% solution) | 0.12 |
| Water | qs to 100 |

Note:
*BTC 2125
**Neodol 25-9
***Anhydrous sodium carbonate

Compositions were also prepared containing the mitigants shown below. The mitigants were separatey added to the above control formulation, the other ingredients remaining constant except for the amount of water. The mitigants and the amounts thereof, were as follows:

|  | Percent |
| --- | --- |
| 1. Unamide ® C-5 | 3 |
| 2. Carbowax ® 6000 (polyoxyethylene containing about 150 moles of condensed ethylene oxide) made by Union Carbide Corp. | 3 |
| 3. Solulan ® L-575 | 3 |
| 4. Lanasan ® CL | 1 |
| 5. Allantoin | 1 |
| 6. 1,6-hexylene glycol | 2 |
| 7. Ammonyx ® SO | 3 |
| 8. 2001 Cerelose | 3 |
| 9. Imidazole | 3 |

The compositions were evaluated for eye irritation using the Draize Test. (See aforementioned NAS Publication 1138). One-tenth of a milliliter of each composition was instilled into the right eye of each of three (3) white albino rabbits, the left eye acting as the control. The rabbits were observed for eye irritation over a 21 day period. The Draize Test employs a scoring system having a maximum score of 110 per rabbit (indicating the most severe damage). The scoring system assesses damage to: the cornea (opacity and area of corneal involvement)—maximum score of 80 per rabbit; the iris—maximum score of 10 per rabbit; and the conjunctivae (redness, chemosis and discharge)—maximum score of 20 per rabbit. The results of the test are set forth in Table I below, wherein the scores reported are the total for the three (3) rabbits after 14 or 21 days, as indicated. A total score for the 3 rabbits after 21 days (or 14 days if that was when the last reading was taken) of less than 20 was considered a "passing score" for purposes hereof, in that a score of less than 20 would indicate that the composition was substantially less irritating than the control composition.

TABLE I

Draize Test (Eye Irritation) Scores for Compositions Containing The Eye Irritation Mitigants Of The Present Invention*

| Mitigant | Total Score (3 Rabbits) | |
|---|---|---|
| | 14 days | 21 days |
| Control | — | 86 |
| Unamide ® C-5 | — | 3 |
| Carbowax ® 6000 | — | 2 |
| Solulan ® CL | 0 | — |
| Lanasan ® CL | — | 19 |
| Allantoin | 12 | — |
| 1,6-hexylene glycol | 20 | 14 |
| Ammonyx ® SO | — | 13 |
| 2001 Cerelose | 2 | — |
| Imidazole | 14 | — |

*A dash (—) indicates that no reading was taken at the time shown

The test results demonstrate that the mitigants of the instant invention significantly reduced the eye irritation of the control formulation.

EXAMPLE 3

Several other reported irritation mitigants were separately incorporated into the control formulation of Example 2 in the manner in which the mitigants of this invention were so incorporated as set forth in Example 2, and the Draize Test results (the test being conducted as outlined in Example 2) of the resulting compositions are presented in Table II.

TABLE II

Draize Test (Eye Irritation) Scores for Compositions Containing Various Other Irritation Mitigants*

| Mitigant (and amount) | Total Score (3 Rabbits) | |
|---|---|---|
| | 14 days | 21 days |
| Control | — | 86 |
| Lauryl Dimethyl amine oxide (3%) | — | 129 |
| Amphoteric Fatty Betaine (Lonzaine ® C) (3%) | — | 141 |
| Benzyl Alcohol (1%) | 128 | 120 |
| Citric Acid (1.5%) | 106 | 74 |
| Sucrose (3%) | 67 | — |
| Polyoxyethylene Sorbitan monopalmitate (Lonzest ® SML20, made by Lonza Chemical Co.) (1%) | — | 142 |
| Sodium N-lauroyl sarcosinate (Maprosyl ® 30, made by Onyx Chemical Co.) (1%) | — | 111 |
| Ascorbic Acid (1%) | 27 | 74 |
| Polypropylene glycol (P-2000, made by Dow Chemical Co.) (1%) | 82 | 81 |
| Lanolin (3%) | 47 | 49 |
| Collagen (3%) | 87 | 59 |
| Vitamin A (0.3%) | 72 | 34 |
| Polyoxyethylene containing about 13 to 34 moles of condensed ethylene oxide (Carbowax ® 1000 made by Union Carbide Corp.) (3%) | — | 32 |
| Aloin (1%) | 70 | 60 |
| Ethoxylated lanolin containing about 25 moles condensed ethylene oxide (Solulan ® 25, made by Amerchol Chemical Co.) (3%) | 28 | — |
| Polyvinyl pyrrolidone (3%) | — | 47 |
| Mannitol (3%) | 31 | — |
| Sorbitol (2.1%) | 45 | — |

*A dash (—) indicates that no reading was taken at the time shown

As can be seen from Table II, other reported irritancy mitigants did not reduce eye irritation in the rabbits to the extent the mitigants of the instant invention did. In fact, in many cases the supposed mitigants actually increased eye irritation when added to the control formulation.

What is claimed is:

1. A disinfectant/cleanser composition having broad spectrum germicidal activity and exhibiting reduced eye irritancy potential which comprises:
   (a) a quaternary ammonium compound;
   (b) a non-ionic surfactant;
   (c) d-limonene;
   (d) an eye irritancy reducing effective amount of a compound selected from the group consisting of: ethoxylated cocodiethanolamide containing an amount of condensed ethylene oxide such that the eye irritancy of said composition is reduced, polyoxyethylene containing an amount of condensed ethylene oxide such that the eye irritancy of said composition is reduced, ethoxylated lanolin containing an amount of condensed ethylene oxide such that the eye irritancy of said composition is reduced, hydrolyzed animal protein, allantoin, 1,6-hexylene glycol, stearyldimethylamine oxide, dextrose sugar and imidazole; and
   (e) water.

2. The composition of claim 1 further comprising a lower aliphatic alcohol.

3. The composition of claim 2 wherein the lower aliphatic alcohol is selected from the group consisting of ethanol, propanol and isopropanol.

4. The composition of claim 2 wherein the quaternary ammonium compound is selected from the group consisting of dialkyl ($C_8$–$C_{12}$) dimethyl ammonium chlorides, n-alkyl ($C_{12}$–$C_{18}$) dimethylbenzyl ammonium chlorides, and n-alkyl ($C_{12}$–$C_{18}$) dimethylethylbenzyl ammonium chlorides; the non-ionic surfactant is selected from the group consisting of condensation products of about 5–30 moles of ethylene oxide with one mole of a compound selected from the group consisting of an alkyl phenol having about 0–15 carbon atoms in the alkyl group, an alkyl amine having about 10–20 carbon atoms in the alkyl group, an aliphatic alcohol having about 9–20 carbon atoms and a fatty acid having about 10–20 carbon atoms; and the lower aliphatic alcohol is selected from the group consisting of ethanol, propanol and isopropanol.

5. The composition of claim 1 or claim 2 comprising about 3 to 10%, by weight, of the quaternary ammonium compound, about 1 to 10%, by weight, of the non-ionic surfactant, about 0.25% to 6%, by weight, of the d-limonene, about 0 to 6%, by weight, of the lower aliphatic alcohol, and about 0.1 to 5%, by weight, of the eye irritancy reducing compound.

6. The composition of claim 4 comprising about 3 to 6% by weight, of the quaternary ammonium compound, about 3 to 8%, by weight, of the non-ionic surfactant, about 3 to 5%, by weight, of the d-limonene, about 2 to 4%, by weight, of the lower aliphatic alcohol, and about 1 to 3%, by weight, of the eye irritancy reducing compound.

7. The composition of claim 5 wherein the ratio of the non-ionic surfactant to the quaternary ammonium compound is about 0.5 to 8:1.

8. The composition of claim 5 wherein the ratio of the non-ionic surfactant to the quaternary ammonium compound is about 2 to 4:1.

9. The composition of claim 5 further comprising a non-phosphate builder.

10. The composition of claim 5 wherein the ethoxylated cocodiethanolamide contains at least about 3 moles of condensed ethylene oxide.

11. The composition of claim 5 wherein the ethoxylated cocodiethanolamide contains about 5 moles of condensed ethylene oxide.

12. The composition of claim 5 wherein the polyoxyethylene contains at least about 40 moles of condensed ethylene oxide.

13. The composition of claim 5 wherein the polyoxyethylene contains from about 100 to 175 moles of condensed ethylene oxide.

14. The composition of claim 5 wherein the ethoxylated lanolin contains at least about 30 moles of condensed ethylene oxide.

15. The composition of claim 5 wherein the ethoxylated lanolin contains from about 100 to 175 moles of condensed ethylene oxide.

16. The composition of claim 5 wherein the quaternary ammonium compound is a mixture of about 50%, by weight, $C_{12}$–$C_{18}$ alkyldimethylbenzyl ammonium chlorides and about 50%, by weight, $C_{12}$–$C_{18}$ alkyldimethylethylbenzyl ammonium chloride, the non-ionic surfactant is an ethoxylated mixture of normal and 2-methyl branched primary $C_{12}$–$C_{15}$ alcohols having about 9 moles of condensed ethylene oxide, and the lower aliphatic alcohol is ethanol.

* * * * *